(12) United States Patent
Waid et al.

(10) Patent No.: US 10,488,387 B2
(45) Date of Patent: Nov. 26, 2019

(54) METHODS AND APPARATUS FOR EXTRACTION OF NAD AND PROTEINS FROM CRUDE OIL AND GAS, DRILL CUTTINGS, CORES AND OTHER HYDROCARBONS AND ORGANICS FOR UNIQUE SPECTRAL IDENTIFICATION

(71) Applicant: RPC, Inc., Atlanta, GA (US)

(72) Inventors: Margaret Cowsar Waid, Houston, TX (US); Charles Carter Waid, Houston, TX (US); Thomas C Cowsar, Houston, TX (US); Scott D Campbell, Dandridge, TN (US); Harlon W Cowsar, Springfield, LA (US)

(73) Assignee: RPC, INC., Atlanta, GA (US)

( * ) Notice: Subject to any disclaimer, the term of this patent is extended or adjusted under 35 U.S.C. 154(b) by 155 days.

(21) Appl. No.: 15/255,123

(22) Filed: Sep. 1, 2016

(65) Prior Publication Data
US 2017/0336382 A1 Nov. 23, 2017

Related U.S. Application Data

(60) Provisional application No. 62/212,854, filed on Sep. 1, 2015, provisional application No. 62/382,761, filed on Sep. 1, 2016.

(51) Int. Cl.
*G01N 33/28* (2006.01)
*G01N 21/33* (2006.01)

(52) U.S. Cl.
CPC ......... *G01N 33/2835* (2013.01); *G01N 21/33* (2013.01); *G01N 33/2823* (2013.01)

(58) Field of Classification Search
CPC . G01N 33/2835; G01N 21/33; G01N 33/2823
See application file for complete search history.

(56) References Cited

U.S. PATENT DOCUMENTS

| 5,858,644 | A | 1/1999 | Chen |
| 9,448,220 | B2 | 9/2016 | Hanby |
| 9,802,183 | B2 | 10/2017 | Hanby |
| 2006/0154328 | A1 | 7/2006 | Bruce et al. |
| 2007/0196826 | A1* | 8/2007 | Ohno ................. C12N 15/1003 435/6.11 |
| 2010/0143995 | A1 | 6/2010 | Erdner-Tindall et al. |
| 2015/0284811 | A1* | 10/2015 | Knight ............... E21B 47/1015 506/2 |

FOREIGN PATENT DOCUMENTS

WO 2013109964 A1 7/2013

OTHER PUBLICATIONS

Dispersing of Petroleum Asphaltenes by Acidic Ionic Liqid and Determination by UV-Visible Spectroscopy Eshagh Rezaee Nezhad, Fariba Heidarizadeh, Sami Sajjadifar, and Zahra Abbasi Journal of Petroleum Engineering (Year: 2013).*

* cited by examiner

*Primary Examiner* — Krishnan S Menon
*Assistant Examiner* — Dwan A Gerido
(74) *Attorney, Agent, or Firm* — Winstead PC (57) ABSTRACT

A method of analyzing crude oil that may include the step of contacting the crude oil with an ionic liquid to form a treated sample. The method may further include determining presence of NAD in the treated sample.

7 Claims, 8 Drawing Sheets

METHODS AND APPARATUS FOR EXTRACTION OF NAD AND PROTEINS FROM CRUDE OIL AND GAS, DRILL CUTTINGS, CORES AND OTHER HYDROCARBONS AND ORGANICS FOR UNIQUE SPECTRAL IDENTIFICATION

RELATED APPLICATION DATA

The present invention claims priority of U.S. Provisional Patent Application Ser. No. 62/212,854, filed Sep. 1, 2015, and of U.S. Provisional Patent Application Ser. No. 62/382,761, filed Sep. 1, 2016, with both applications herein incorporated by reference.

BACKGROUND OF THE INVENTION

1. Field of the Invention

The present invention relates to methods, apparatus and products for analyzing chemical compositions. In another aspect, the present invention relates to methods, apparatus and products for comparing various chemical compositions. In even another aspect, the present invention relates to methods, apparatus and products for extraction of NAD and proteins from crude oil and gas, drill cuttings, cores and other hydrocarbons and organics for unique spectral identification. In still another aspect, the present invention relates to methods, apparatus and products for comparing various chemical compositions to show if part or all of the various chemical compositions had a common source or if one was derived from the either.

2. Description of the Related Art

The Jurassic Age (180 million to 140 million years ago) and the Cretaceous Age (140 million to 65 million years ago) were a very good ages for oil formation. For the most part, the age of source rock has been determined by analysis of the geological formations. A news release by Stanford University on 08/04/94 announced a "biological" means of determining age by investigating compounds that may be present in oil from a flowering plant called "oleanane". In the dozen years since that time many hours of research work have gone into determining how to "find" oleanane. While the Stanford press release and activity leads to an expectation that the NAD (DNA and RNA) fragments contained in crude oil and hydrocarbons may yet exist in the crude oil and hydrocarbons produced from their remains. However, in the dozen years since there has been no luck in finding any NAD in crude oil.

U.S. Pat. No. 5,589,349 issued Dec. 31, 1996 to Shinzaki et al. discloses a method of enzymatic analysis utilizing a color-development signal amplification system associated with enzymatic cycling of NAD-NADH interconversion in the presence of dehydrogenase and its substrate, wherein the dehydrogenase is selected from the group consisting of alcohol dehydrogenase derived from Zymomonas and amino acid dehydrogenase derived from thermophilic microorganisms is disclosed. The use of alcohol dehydrogenase derived from Zymomonas provides an extremely higher detection sensitivity than that in the conventional method. The use of amino acid dehydrogenase derived from thermophilic microorganisms improves reliability of the method for a longer period of time than that in the conventional method.

U.S. Pat. No. 5,858,644 issued Jan. 12, 1999 to Chen discloses a method for detecting an analyte in a sample uses both the specificity of an enzymatic reaction and the separation power of capillary electrophoresis. In general, the method comprises: (1) subjecting a first aliquot of the sample to an analytical technique such as capillary electrophoresis, which generates a first output such as an electropherogram; (2) reacting a second aliquot of the sample in an enzyme-catalyzed reaction converting the analyte into a product, the product being detectable by the analytical technique; (3) subjecting the second aliquot to the analytical technique to generate a second output; (4) in the case of electrophoresis, measuring the absorbance of the first and second outputs (electropherograms) as a function of migration distance along the electropherogram at at least one wavelength at which either the analyte or the product absorbs to produce a first absorbance scan and a second absorbance scan; and (5) comparing the first absorbance scan with the second absorbance scan to detect the analyte. The reaction can involve a coenzyme and the analytical technique can be directed to the coenzyme. Alternatively, at least two enzymes can be used, the first enzyme generating a first product that is then acted upon by the second enzyme.

U.S. Patent Application Publication No. 2006/0154328 published Jul. 13, 2006 by Bruce et al., relates to ionic liquids and their use as solvents in biocatalysis. According to a first aspect of the invention there is provided a method of carrying out an enzyme-catalysed reaction comprising providing a liquid reaction medium which comprises an ionic liquid including an ion which comprises a functional group selected from the group consisting of alkenyl, hydroxyl, amino, thio, carbonyl and carboxyl groups, providing in the liquid reaction medium an enzyme and a substrate for the enzyme, and allowing reaction of the substrate to occur.

U.S. Patent Application Publication No. 2010/0143995 published Jul. 10, 2010 by Erdner-Tindal et al., discloses a process for fermentive preparation of alcohols and recovery of product using liquid-liquid extraction, wherein at least one ionic liquid is used as the extractive solvent.

SUMMARY OF THE INVENTION

The present invention provides that NAD (DNA and RNA) as well as associated proteins in the UV-Vis spectrum of crude oil is indicated by the absorbance spectral peak at AU 260 nanometers. A deuterium light source with an OEM Avantes UV-Vis Spectroscope was used to determine the clearly indicated spectral peak. A Master Solution using a particular ionic liquid was used to activate and extract this NAD at 260 nm to NADH with a peak at 340 nm. There is a protein peak at 230 nm as well as at 280 nm and well known ratios used in DNA and RNA analysis to determine the purity of the NAD around the 260 nm peak. The purity analysis indicates primarily the amount of protein contained in the spectrum that is obscured by the NAD spectrum.

BRIEF DESCRIPTION OF THE DRAWINGS

The following drawings illustrate some of the many possible embodiments of this disclosure in order to provide a basic understanding of this disclosure. These drawings do not provide an extensive overview of all embodiments of this disclosure. These drawings are not intended to identify key or critical elements of the disclosure or to delineate or otherwise limit the scope of the claims. The following drawings merely present some concepts of the disclosure in a general form. Thus, for a detailed understanding of this disclosure, reference should be made to the following detailed description, taken in conjunction with the accompanying drawings, in which like elements have been given like numerals.

DETAILED DESCRIPTION OF THE INVENTION

The present invention provides that NAD (DNA and RNA) as well as associated proteins in the UV-Vis spectrum of crude oil is indicated by the absorbance spectral peak at AU 260 nanometers. A deuterium light source with an OEM Avantes UV-Vis Spectroscope was used to determine the clearly indicated spectral peak. A Master Solution using a particular ionic liquid was used to activate and extract this NAD at 260.

Figure 1:
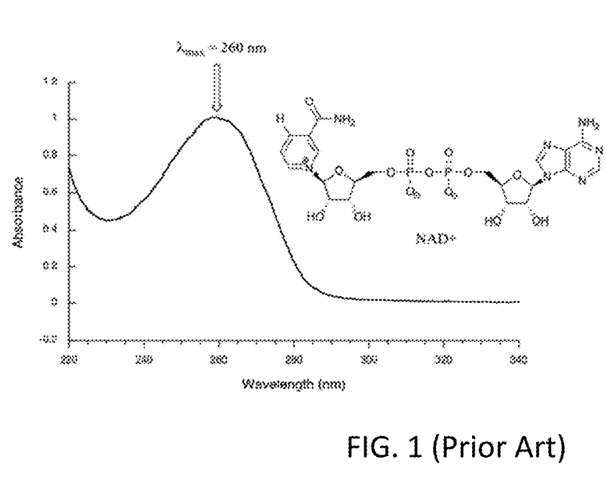
FIG. 1 illustrates a typical AU 260 peak in the UV absorbance spectrum of organic matter along with chemical structure of NAD.
Figure 2:
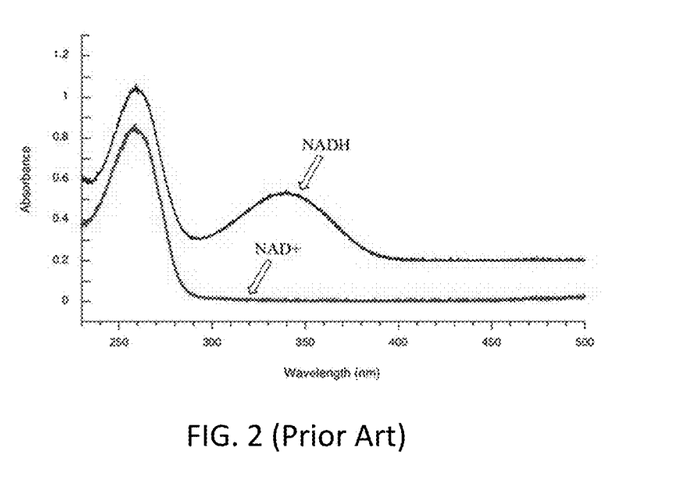
FIG. 2 shows a UV absorbance spectrum illustrating NAD with its usual AU 260 nm spectral peak and the related NADH spectrum with its usual AU 340 spectral peak.
Figure 3:
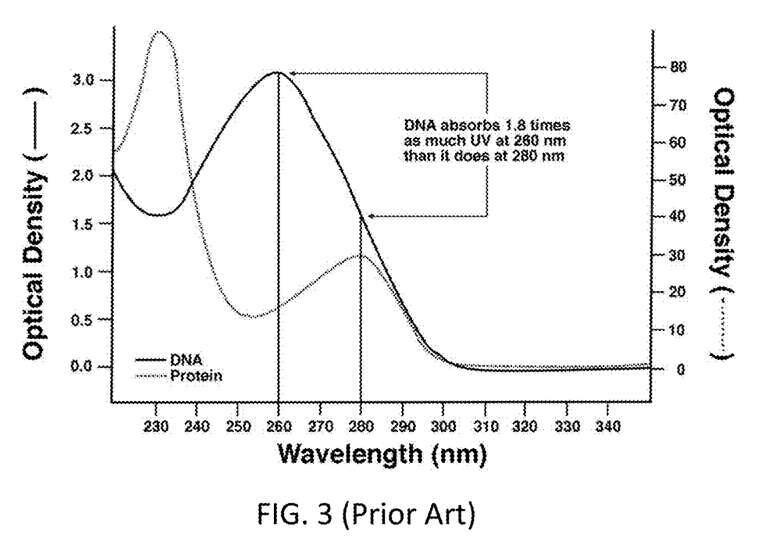
FIG. 3 illustrates a spectral peak of NAD which is DNA and RNA at AU 260 nm and a two spectral peaks for protein at AU 230 nm and at AU 280 nm a means of determining purity of NAD.

The nm to NADH with a peak at 340 nm. There is a protein peak at 230 nm as well as at 280 nm and well known ratios used in DNA and RNA analysis to determine the purity of the NAD around the 260 nm peak. The purity analysis indicates primarily the amount of protein contained in the spectrum that is obscured by the NAD spectrum. Attention is directed to FIGS. 1, 2, and 3.

By using the Master Solution with samples of crude oil, unique DNA/RNA/Protein profiles of the crude sample may be generated. By further planned extraction work for comparison with other crude oils that may have come from different compartments in the same well that was drilled or from compartments from wells drilled in the same reservoir, the unique DNA and RNA and Proteins contained in the samples are used to determine if the crude oil has the same profile or not.

Figure 4:
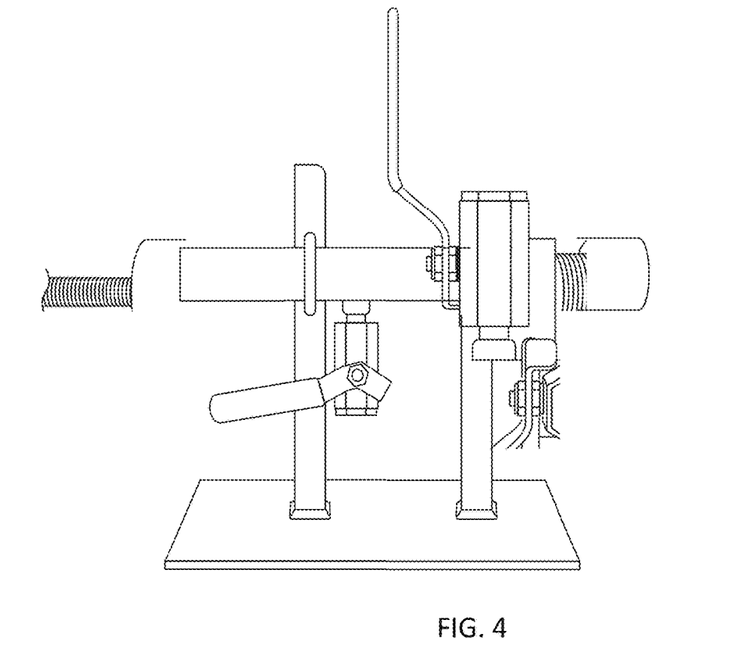
FIG. 4 is a semi-automated means of cleaning drill cutting, crushing drill cuttings, treating the drill cuttings with ionic liquid and recovering the treated fluids at each stage of the process so that they can be examined with the UV-Vis and NIR spectroscopes.
Figure 10:
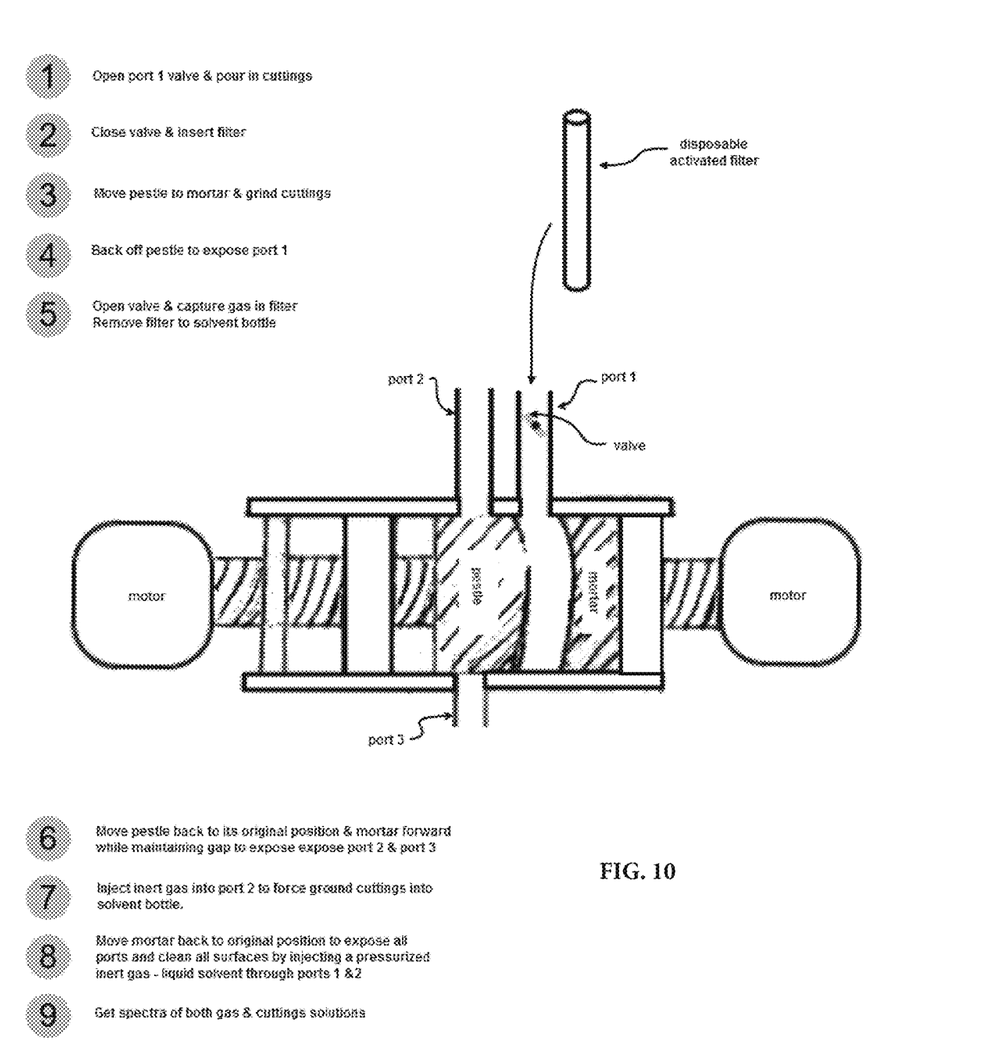
FIG. 10 is a drawing sketch of an invention for an improved version of the instrument in FIG. 4.

This same analysis may be used on produced oil, dry and wet gas, and produced water. Drill cuttings obtained during the drilling of a well from each depth (say each 10 feet) are first cleaned of any hydrocarbon and organic matter and water that may have been in the drilling mud, either from drilling a prior well, or from drilling the same well. A special process is used to clean the drill cuttings and to check to make sure that they are clean. Then the drill cuttings are crushed or ground in a special fixture that is disclosed in this patent application. Reference is now made to FIG. 4 and FIG. 10.

The contents of the drill cuttings are then processed using the Master Solution. It should be noted that the drill cuttings contain 100 percent of the "live" oil and water rather than the "dead" oil and water that may be contained in drilling mud or flashed produced samples. Some drill cuttings will contain no oil or gas. Some will contain water only. Some may contain as much as 95 percent water or more. As drill cuttings come to the surface and are collected at the surface, this is the way that the pure hydrocarbon containing the pure DNA and RNA and protein of the samples are brought to the surface.

When a sample 'bag" or container is brought into the mini-lab at the well site, the drill cuttings from that sample "bag" are mixed up and then divided so that representative samples from the same bag may be analyzed in multiple ways. One way is to analyze the fluids in the bags, another is to analyze crushed drill cuttings taken from the bags using XRD and XRF for minerals that are present in the rocks. In the case of the analyzing the fluids, the drilling mud that the cuttings are in is first analyzed using spectroscopes to determine the UV-Vis and NIR spectrum of the drilling mud. Then one will know if the drill cuttings have been cleaned. Similarly, this will be done prior to XRD and XRF analysis with representative samples of the drill cuttings from the same bag. Other of the drill cuttings from the same bag are labelled and are preserved for future analysis and future replication of the same process.

In the process of analyzing the fluid contents of the drill cuttings only a very small amount of crude oil is required as only a very small amount of the fluid containing DNA and RNA samples is required to get a "DNA accurate" fingerprint or spectral profile from real DNA and RNA of the particular crude oil and water from that depth. The same small 2 mm path length cuvette is used in the NIR spectroscope to get a water spectrum and determine the water concentration. Then the cuvette is placed in the UV-Vis spectroscope and the AU 260 nm peak is found if present. If there is no hydrocarbon present, then there is no peak at AU 260. A spectrum is taken however so one will have a complete spectrum profile at that depth where no water is present. For example, since this work is done on site and in real-time, concurrently with drilling, one will be able to compare the spectrum of a hydrocarbon-producing Wilcox with a non-hydrocarbon producing-Wilcox and know whether the owner wants to continue drilling or not or and where the owner wants to set casing, etc. And it will even be possible to determine if formations that are currently geologically known as Wilcox and produce fluids are producing fluids of the same genetic DNA and RNA as well as proteins as these are seen in the UV-Vis spectrum for each sample that is processed and analyzed by these methods.

All of the applications of Spectral Fingerprinting of Hydrocarbons and Other Organics that were listed in the earlier provisional filed on Sep. 1, 2015, may be used with this spectral analysis, methods, etc., that are described here.

And, as well, any DNA and RNA and protein that is obtained in any other way may be processed in this manner using the same Master Solution and ionic liquids. The only thing that may be changed are the solvents that are used to capture the DNA and RNA. Furthermore, the "designer" ionic liquids may be changed in order to target certain components or chemicals or compounds that are contained in the NAD peak at AU 260 or the protein peaks and other NAD or NADH or epsilon-NAD peaks that appear in the spectrum.

Figure 5:
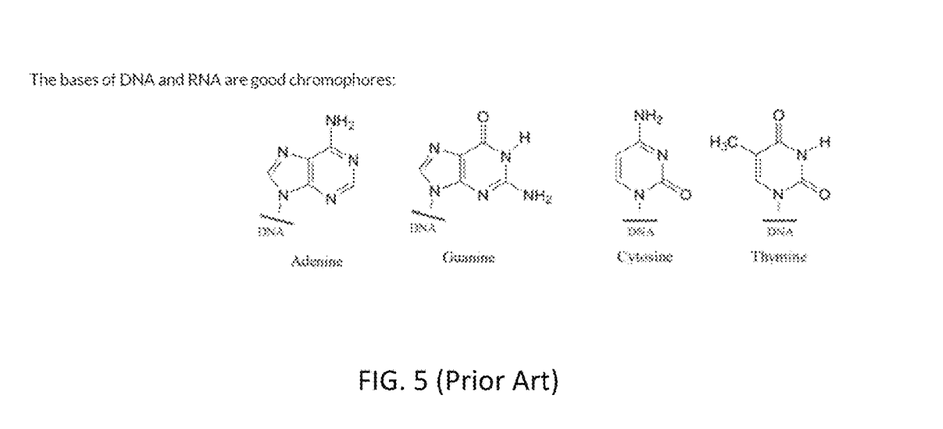
FIG. 5 shows the bases of life that are contained in NAD for all organic matter that has DNA and RNA.

For clarity, it is noted that what is contained in the AU 260 NAD peak are at this time known to be: a sugar group, a phosphate group, and bases. The bases of DNA and RNA are good chromophores: Adenine, Guanine, Cytosine, and Thymine. See, FIG. 5.

The alkanes are found in the proteins at around AU 230 such as: heptane, hexane, pentane, cyclopentane, cyclohexane, 2,2,4-trimethylpentane, and decalin. For the proteins at around AU 280 we find ethyl acetate, 2-ethoxyethanol, and aromatic hydrocarbons such as benzene.

According to one non-limiting embodiment of the present invention the sugars in the DNA and RNA show up in the ethenes and ethylenes and ethanol. The polyethylenes become plastics such as PVC. The phosphates can be produced as fertilizers in refiners as ammonium phosphate.

Thus, according to non-limiting embodiments of the present invention, the DNA and RNA show up in refined products. In the following document, we pay special attention to the section on General Chromophores and the discussion on 280 nm to 300 nm.

Both NAD+ and NADH absorb at 260 nm. However NADH, unlike NAD+, has a second absorbance band with $\lambda max=340$ nm and $\varepsilon=6290$ L*mol−1*cm−1. The figure below shows the spectra of both compounds superimposed, with the NADH spectrum offset slightly on the y-axis. Please see FIG. 2.

Figure 6:
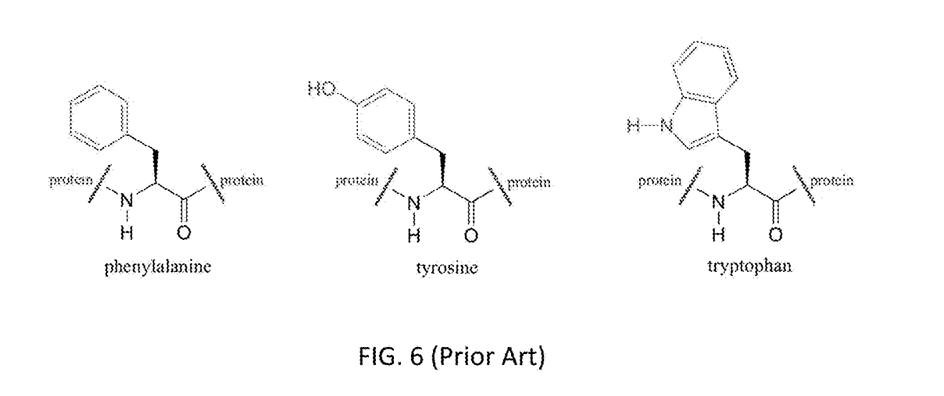
FIG. 6 illustrates how these typical proteins may change conformationally, such as partial unfolding as its environment changes, thus causing its UV spectrum to be altered.

UV spectroscopy is also very useful in the study of proteins. Proteins absorb light in the UV range due to the presence of the aromatic amino acids tryptophan, phenylalanine, and tyrosine, all of which are chromophores. Please See FIG. 6.

Molecules such as FAD (flavin adenine dinucleotide), NADH and NAD are important coenzymes of proteins involved in electron transfer reactions (RedOx reactions). They can be conveniently assayed by using their UV/Vis absorption: 438 nm (FAD), 340 nm (NADH) and 260 nm (NAD).

Chromophores in genetic material: The absorption of UV light by nucleic acids arises from transitions of the purine (adenine, gaunine) and pyrimidine (cytosine, thymine, uracil) bases that occur between 260 nm and 275 nm. The absorption spectra of the bases in polymers are sensitive to pH and greatly influenced by electronic interactions between bases. See FIG. 6.

It is well understood in biochemistry frequently to use UV spectroscopy to study conformational changes in proteins— how they change shape in response to different conditions. When a protein undergoes a conformational shift (partial unfolding, for example), the resulting change in the environment around an aromatic amino acid chromophore can cause its UV spectrum to be altered. See FIG. 6.

Figure 7:
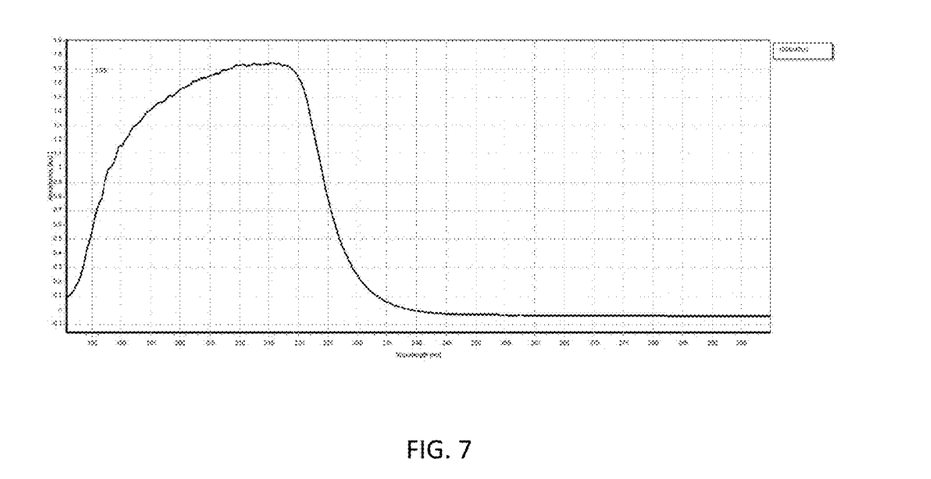
FIG. 7 is the UV-Vis spectrum of spectroscopically pure DCM (dimethylchloride) that may be used as a solvent in part for cleaning drill cuttings and soil samples for heavy crude oils.

FIG. 7 is the spectrum of the DCM (dimethylchloride) that is being used as a solvent in part for cleaning drill cuttings and soil samples and in conjunction with the ionic liquid that may be used as an extractant or catalyst reaction. The ionic liquids may be similar to Lewis Acids. They are designer ionic liquids that are also designed to accommodate for the water that may be in the oil or gas or other liquids. Usually this is a problem for Aluminum Chloride that may be used with tetrachloride as a catalyst for the visible range. Aluminum Chloride and Tetrachloride combination are not good for DNA and RNA extraction because the spectra cover up the chromophores and spectra that are recognized as the DNA and RNA spectra and proteins in the UV range. So this is not the same as the Hanby claims in other patents and literature. Hanby deals only with the visible range and does not recognize anything as NAD (DNA and RNA) and proteins, such as NAD and NADH or NADPH or other forms of epsilon NAD that may be in the visible range.

As with other DNA and RNA information, enzymes may be injected to reveal new information by those skilled in the art. Also the letters that in order describe the chromosomes recognized by those skilled in the art may be developed as time goes on.

Some minerals such as pyrite that are contained in drill cuttings and cores may result in pyridine or other chemicals to be contained in the fluids in the drill cuttings. Pyridine and other related chemical derivatives of pyrite may cause the NADH to shift its peak from the usual 339 nm or 340 nm in the uv absorbance spectrum to any value for example from 325 nm to 339 nm or 340 nm. For example 335 nm has been recorded as a spectral peak for some of the hydrocarbons extracted from clean drill cuttings for the NADH rather than 340 nm which has been seen for produced fluids from the same well. This may well prove to be a distinguishing characteristic for certain hydrocarbons obtained from some wells.

A number of tests have been run for crude oils obtained from wells which may have been produced or obtained from downhole formation tester samples. Indeed, also a number of tests have been run for crude oils that have been obtained from drill cuttings.

CAMO software (such as CAMO Unscrambler X) will be used to correlate those crude oils or hydrocarbons that have similar or like profiles. The software will also be used to separate comingled oils or gases that are mixtures of other oils and gases. This will be based on having DNA and RNA and protein profiles of each of the components of the mixtures as well as on any other characteristics of the profiles that are distinguishing.

Figure 8:
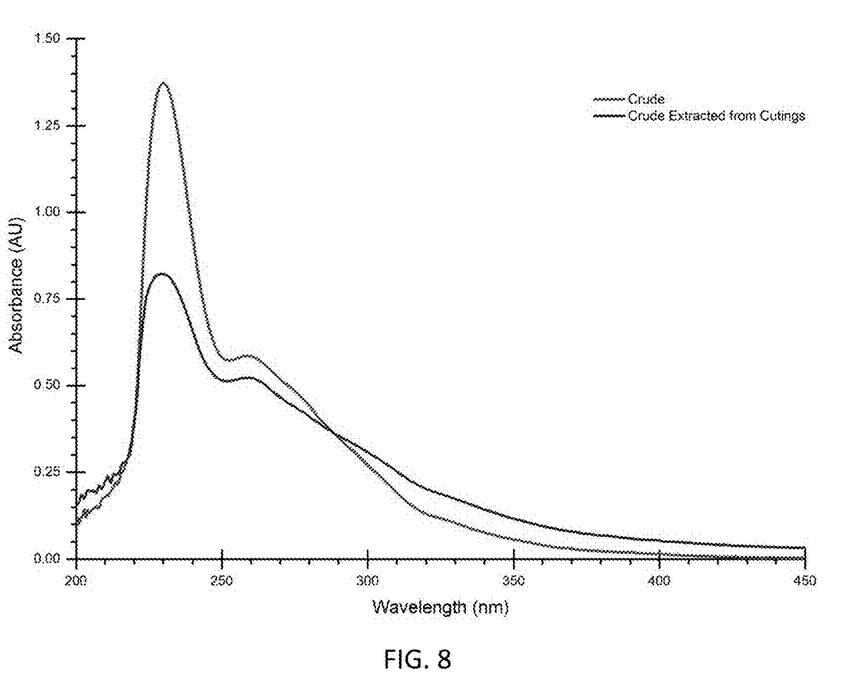
FIG. 8 shows for comparison the UV-Vis absorbance spectrum of a sample of a crude oil that is being produced from a well (red) and the UV-Vis absorbance spectrum of a sample of crude oil that has been removed from clean drill cuttings from a certain depth in the same well.

In FIG. 8, this red colored spectrum is a UV-VIS spectroscopic image made from produced crude oil. In the blue colored spectrum is a UV-VIS spectroscopic image made from crude oil taken from cleaned cuttings that we believe the produced oil is coming from. Both of them have the hydrocarbon DNA and RNA peak at AU 260 nm. We want to show that these two crude oils have the same DNA and RNA and proteins.

Figure 9:
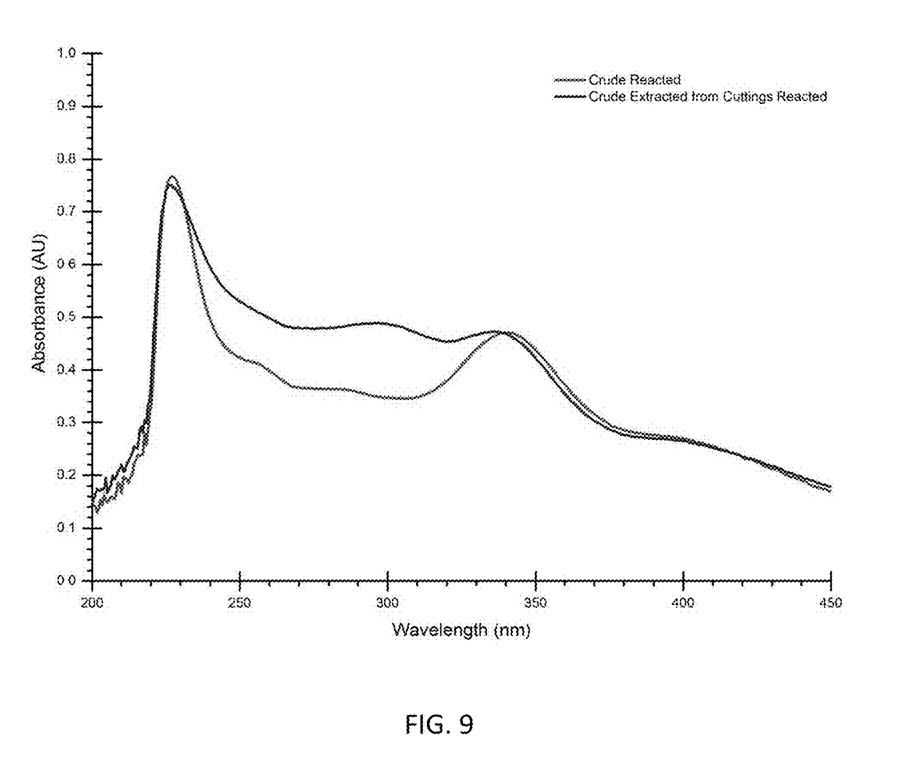
FIG. 9 shows for comparison the same crude oils that were shown in FIG. 8 after they have been reacted with a certain amount of the ionic liquid that has changed the absorbance spectrum of both of them.

In FIG. 9, see the red spectrum in which the produced crude has reacted with a certain amount of the prepared Master Solution which contains the ionic liquid which has changed its spectrum. The NADH peak at 340 nm has been produced from the NAD at 260 nm that contains the DNA and RNA, some NADH, and some of the proteins from the protein peak at 230 nm and the protein peak that was obscured at 280 nm. The blue spectrum which contains the crude oil extracted from the clean cuttings has also reacted with a certain amount of the prepared Master Solution which contains the ionic liquid has also changed its spectrum. The NADH peak at 335 nm shows that the NAD at 260 nm that contains the DNA and RNA and some of the proteins from the protein peak at 230 nm and the protein peak that was obscured at 280 nm. The reason that there is a 335 nm peak rather than a 340 nm peak is due to the fact that there is something else in the cuttings such as pyridine that has caused the peak to shift. However, the UV spectrum for both contains both red and blue curves that overlay, thus confirming that the produced crude oil and the crude oil that came from the cuttings are in the same geological compartment. In fact, the protein peak at 230 now matches as well. This match shows that we can determine which compartment that the produced crude came from by studying the DNA and RNA and proteins and that were in the two crude oils after extracting the DNA and RNA and proteins from the 260 nm peak. This is common to all organic materials that possess DNA and RNA with a 260 nm peak that includes a sugar group, a phosphate group, and common genetic bases that pair.

Experimentation with different geological compartments will help to put the drill cuttings on proper depth and determine any minerals that may impact the study of the NADH. The mineralogy of the drill cuttings is determined by studying drill cutting samples taken at the same time from the same depth as part of the same representative sample. The XRD/XRF is used to make this determination as well as other information of interest such as the salinity of the water in the drill cuttings.

In the process of removing the fluid from the clean drill cuttings, and NIR spectroscope is used to study the fluids to determine what water is present and how much of the fluid is water. The Master Solution mixture is also used to take the water from fluid contained within the cuttings. Everything that has been done with drill cuttings can also be done with cores, both normal and side-wall cores, or even cores obtained by bullet perforating. It does not matter how old the cores/cuttings are as the DNA and RNA and proteins remain in the cores/cuttings. Similar analysis may be used for produced wells or from samples obtained from formation testers or drill stem tests. Also for plug-and-abandon wells, the same testing may be done to make sure that packers and pipes in and around the wells are secure and there are no leaks.

Also, the same technology may be used to test oil which is contained in soil and water that gets there from leaks from wells, pipe lines, ships, etc.

In addition to the use of XRD/XRF as part of the mini-lab that is used in a field location for on-site, near real-time analysis or in a laboratory for more detailed analysis, we will also have other sensors and methods that from the clean cuttings will give us irreducible water saturation, resistivity of fluids, dielectric of fluids, viscosity, and other information commonly obtained from mud logging and PVT laboratory analysis of fluids and rocks. This will mean that there will be much less need to run wireline and LWD logs which are very expensive and have huge charges for lost in hole (LIH) and that are run with much risk for often less information.

FIG. 10 below is a sketch of the latest invention of the cuttings/rock crusher.

Figure 11:
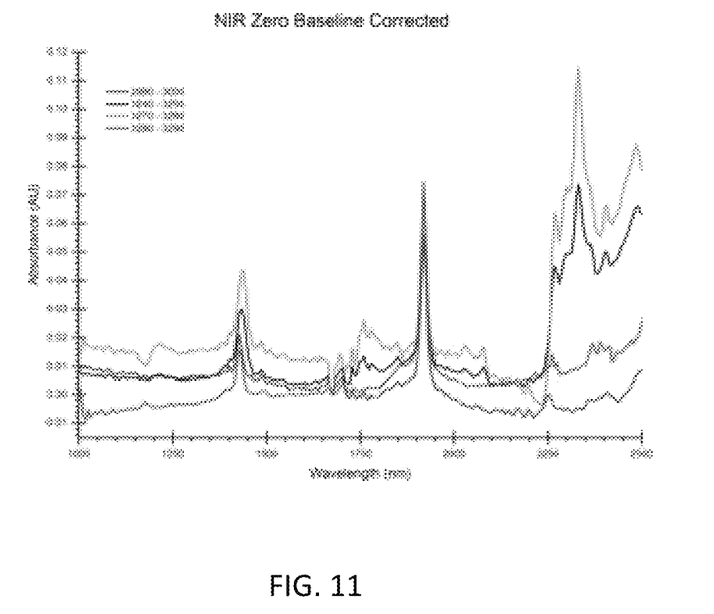
FIG. 11 shows UV-Vis absorbance spectrum for fluids obtained from cleaned drill cuttings.
Figure 12:
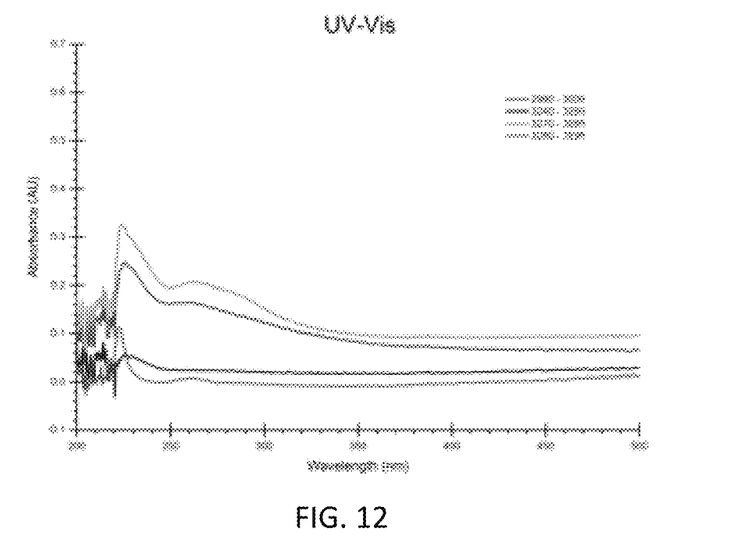
FIG. 12 shows NIR absorbance spectrum for the same cleaned drill cuttings as in FIG. 11.

FIG. 11 shows UV-Vis for fluids obtained from cleaned drill cuttings. FIG. 12 shows NIR for fluids obtained from cleaned drill cuttings for the same given depths of cuttings. By studying both the UV-Vis and the NIR, it is possible to see whether there is water and hydrocarbons at each by looking at the peaks as well as the NAD, and then by further analysis of the UV absorbance spectra by addition of the Master Solution in specified amounts. Note that at 3240-3250 (blue), there is no NAD peak at 260 nm and thus no hydrocarbon.

Non-limiting examples of suitable ionic liquids includes:
1-Ethyl-3-Methylimidazolium trifluoromethanesulfonate
1-Butyl-3methylimidazolium hexafluorophosphate
1-Ethyl-3methylimidazolium Hexafluorophosphate
[HN222][Al2Cl7] (3:1:1 ratio) Designer ionic liquid prepared by private company.
There are other ionic liquids. Ones that we will use will be designed for the particular applications. This is the solvent we are using. But there are other organic solvents depending on what one wants to extract from the NAD, for example:
Dichloromethane (stabilized with 2-Methyl-2-butene)
Here are some of the oils being used in the analysis:

| Material identity | Crude Oil | |
| --- | --- | --- |
| Trade Name(s) | Oriente, Cano Limon, Line 63, Shell-Ventura, SJV Light, Rainbow, West Texas Inter-Cushing, Peace River-Canadian, Federated Crude-Canadian, Pembina Crude-Canadian, Forcados, Cabinda, Basrah Light, Basrah, Arab Medium, Elang Crude, Girassol | |
| Other Name(s) | Earth Oil, Petroleum Oil, Rock Oil, Zafiro | |
| Chemical Description | This material is a C1 to C50 hydrocarbon liquid which contains approximately .9 to 2.8 wt % sulfur compounds | |
| Manufacturer's Address | BP West Coast Products LLC Carson Business Unit 1801 E. Sepulveda Boulevard Carson, California 90749-6210 | BP West Coast Products LLC Cherry Point Business Unit 4519 Grandview Road Blaine, Washington 98230 |

According to one non-limiting embodiment of the present invention, there is provided a process for cleaning and extraction of NAD as follows:
Step 1—Cleaning Samples
Record Sample Depth and label 20 ml Vial
Weigh sample and place in Vial
Dilute with Solvent
Shake
Allow fine grains to settle
Obtain spectra and record in database
Step 2—Extraction
Remove cuttings from Vial in step 1
Crush cuttings to fine powder
Weigh sample and place in Vial
Dilute with Solvent
Shake
Allow fine grains to settle
Obtain spectra and record in database
Remove liquid from Vial and place into another Vial
Wait 4 hours
Obtain Spectra and record in database
Dilute if spectra is saturated
Calculate PPM of Hydrocarbon concentration Measure volume of Ionic Liquid (based on concentration) and place Vial
Shake for 90 seconds
Obtain Spectra and record in database analysis

We claim:

1. A method of analyzing a well sample comprising:
contacting the well sample with an ionic liquid to form a treated sample, wherein NADH in the treated sample is extracted from NAD in the well sample upon contact with the ionic liquid;
determining whether hydrocarbons are present in the treated sample, wherein the determining comprises:
obtaining a spectra of the treated sample;
comparing the spectra of the treated sample with known spectra corresponding to known geological compartments;
determining peaks in the spectra of the treated sample;
determining if the hydrocarbons in the treated sample is from a same geological compartment as one of the known geological compartments based, at least in part, on a correlation between the peaks in the spectra of the treated sample and at least one peak of the known spectra;
identifying a first peak that corresponds to NADH from the known spectra of a specific compartment of the known geological compartments;
identifying a second peak in the spectra of the treated sample; and
determining if a first match exists between the first peak and the second peak, wherein matching indicates the NADH is present in both the specific compartment and the treated sample.

2. The method of claim 1, wherein the determining comprises:
identifying a third peak that corresponds to a protein from the known spectra of the specific compartment of the known geological compartments;
identifying a fourth peak in the spectra of the treated sample;
determining if a second match exists between the third peak and the fourth peak, wherein matching indicates the protein is present in the specific compartment and the treated sample; and
responsive to the first match and the second match, determining if the well sample is from one of the known geological compartments.

3. The method of claim 1, wherein the well sample comprises drill cuttings.

4. The method of claim 3, comprising:
performing X-Ray Fluorescence (XRF) or X-Ray Diffraction (XRD) on the drill cuttings; and
determining mineralogy of the drill cuttings.

5. The method of claim 1, wherein the spectra is obtained via ultraviolet-visible (UV-Vis) or near-infrared (NIR) spectroscopy.

6. The method of claim 1, wherein the ionic liquid comprises an ion and a functional group selected from the group consisting of alkenyl, hydroxyl, amino, thio, carbonyl or carboxyl groups.

7. The method of claim 1, comprising diluting the well sample with dichloromethane.

* * * * *

UNITED STATES PATENT AND TRADEMARK OFFICE
CERTIFICATE OF CORRECTION

PATENT NO. : 10,488,387 B2
APPLICATION NO. : 15/255123
DATED : November 26, 2019
INVENTOR(S) : Margaret Cowsar Waid et al.

Page 1 of 1

It is certified that error appears in the above-identified patent and that said Letters Patent is hereby corrected as shown below:

In the Specification

Column 3, Line 27   Delete "(dimethylchloride)"

Column 3, Lines 41-42   Replace "UV-Vis absorbance spectrum for fluids obtained from cleaned drill cuttings" with "NIR absorbance spectrum for the same cleaned drill cuttings as in Figure 12"

Column 3, Lines 43-44   Replace "NIR absorbance spectrum for the same cleaned drill cuttings as in Figure 11" with "UV-Vis absorbance spectrum for fluids obtained from cleaned drill cuttings"

Column 5, Line 66   Delete "(dimethylchloride)"

Column 8, Lines 6-7   Replace "UV-Vis for fluids obtained from cleaned drill cuttings" with "NIR for fluids obtained from cleaned drill cuttings for the same given depths of cuttings"

Column 8, Lines 7-8   Replace "NIR for fluids obtained from cleaned drill cuttings for the same given depths of cuttings" with "UV-Vis for fluids obtained from cleaned drill cuttings"

Signed and Sealed this
Eighteenth Day of February, 2020

Andrei Iancu
*Director of the United States Patent and Trademark Office*